United States Patent
Ogura et al.

(10) Patent No.: US 9,198,946 B2
(45) Date of Patent: Dec. 1, 2015

(54) GREEN TEA EXTRACT

(71) Applicant: Kao Corporation, Tokyo (JP)

(72) Inventors: Yoshikazu Ogura, Tokyo (JP); Susumu Ohishi, Tokyo (JP); Masahiro Fukuda, Tokyo (JP); Hirokazu Takahashi, Tokyo (JP); Eri Itaya, Tokyo (JP); Atsushi Konishi, Tokyo (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/029,259

(22) Filed: Sep. 17, 2013

(65) Prior Publication Data

US 2014/0113011 A1   Apr. 24, 2014

Related U.S. Application Data

(62) Division of application No. 12/971,555, filed on Dec. 17, 2010, now Pat. No. 8,574,655, which is a division of application No. 10/532,727, filed as application No. PCT/JP03/13700 on Oct. 27, 2003, now Pat. No. 7,883,734.

(30) Foreign Application Priority Data

| Oct. 28, 2002 | (JP) | 2002-313080 |
| Oct. 28, 2002 | (JP) | 2002-313081 |
| Nov. 22, 2002 | (JP) | 2002-339735 |
| Nov. 29, 2002 | (JP) | 2002-348791 |
| Nov. 29, 2002 | (JP) | 2002-348796 |
| Mar. 27, 2003 | (JP) | 2003-086895 |

(51) Int. Cl.

| A61K 36/82 | (2006.01) |
| A23F 3/16 | (2006.01) |
| A23F 3/20 | (2006.01) |
| A23F 3/36 | (2006.01) |
| A23F 3/38 | (2006.01) |
| A23L 1/30 | (2006.01) |
| A23L 2/80 | (2006.01) |

(52) U.S. Cl.
CPC . *A61K 36/82* (2013.01); *A23F 3/16* (2013.01); *A23F 3/163* (2013.01); *A23F 3/20* (2013.01); *A23F 3/36* (2013.01); *A23F 3/366* (2013.01); *A23F 3/385* (2013.01); *A23L 1/3002* (2013.01); *A23L 2/80* (2013.01)

(58) Field of Classification Search
CPC ............. A61K 36/82; A23F 3/16; A23F 3/20; A23F 3/163; A23F 3/36; A23F 3/366; A23F 3/385; A23L 1/3002; A23L 2/80
USPC .............................................. 426/597, 330.3
See application file for complete search history.

(56) References Cited

U.S. PATENT DOCUMENTS

| 4,324,840 A | 4/1982 | Katz |
| 4,331,694 A | 5/1982 | Izod |
| 4,495,210 A | 1/1985 | Green et al. |
| 4,613,672 A | 9/1986 | Hara |
| 4,938,977 A | 7/1990 | Gehrig et al. |
| 4,946,701 A | 8/1990 | Tsai et al. |
| 5,260,437 A | 11/1993 | Ramaswamy |
| 5,318,986 A * | 6/1994 | Hara et al. ............... 514/456 |
| 8,187,656 B2 * | 5/2012 | Konishi .................... 426/597 |
| 2003/0082273 A1 | 5/2003 | Iwasaki et al. |
| 2004/0028793 A1 | 2/2004 | Inaoka et al. |

FOREIGN PATENT DOCUMENTS

| DE | 10036011 | 2/2001 |
| EP | 0 167 399 A2 | 1/1986 |
| EP | 1 297 757 A1 | 4/2003 |
| JP | 46-39058 | 11/1971 |
| JP | 59-219384 | 12/1984 |
| JP | 1-45345 | 10/1989 |
| JP | 2-22755 | 5/1990 |
| JP | 4-20589 | 1/1992 |
| JP | 4-300836 | 10/1992 |
| JP | 4-352726 | 12/1992 |
| JP | 6-128168 | 5/1994 |
| JP | 6-142405 | 5/1994 |
| JP | 7-313062 | 12/1995 |
| JP | 8-70772 | 3/1996 |
| JP | 8-109178 | 4/1996 |
| JP | 10-4919 | 1/1998 |
| JP | 10-67771 | 3/1998 |
| JP | 11-140092 | 5/1999 |
| JP | 2000-166466 | 6/2000 |
| JP | 2002-153211 | 5/2002 |
| WO | 02/39822 | 5/2002 |

OTHER PUBLICATIONS

English Translation for JP 10-004919 published Jan. 13, 1998.*
English Translation for JP 06-142405 published May 1994.*
Extended European Search Report issued Oct. 6, 2011, in Patent Application No. 11173763.1.
Extended European Search Report issued Oct. 6, 2011, in Patent Application No. 11173762.3.

(Continued)

*Primary Examiner* — Anthony Weier
(74) *Attorney, Agent, or Firm* — Oblon, McClelland, Maier & Neustadt, L.L.P.

(57) ABSTRACT

A process for selectively removing caffeine from a caffeine-containing catechin composition, which includes dissolving the caffeine-containing catechin composition in a 9/1 to 1/9 by weight mixed solution of an organic solvent and water, and then bringing the resultant solution into contact with activated carbon alone or with activated carbon and also acid clay or activated clay; and a packaged beverage containing such a decaffeinated composition.

8 Claims, No Drawings

(56) References Cited

OTHER PUBLICATIONS

Communication pursuant to Article 94(3) EPC issued Oct. 5, 2012, in Application No. 03 758 933.0-2114.
Office Action issued Mar. 4, 2013 in European Patent Application No. 03 758 933.0.
Communication pursuant to Article 94(3) EPC issued Oct. 5, 2012, in Application No. 11 173 762.3-2114.
Derwent Abstract for JP 46-39058 published Nov. 1971.
Communication pursuant to Article 94(3) EPC issued Oct. 5, 2012, in Application No. 11 173 763.1-2114.
Patent Abstracts of Japan, JP 10-067771, Mar. 10, 1998.

* cited by examiner

GREEN TEA EXTRACT

CROSS-REFERENCE TO RELATED APPLICATIONS

The present application is a divisional of U.S. Ser. No. 12/971,555, filed on Dec. 17, 2010 now U.S. Pat. No. 8,574,655, which is a divisional of U.S. Ser. No. 10/532,727, filed on Apr. 27, 2005 now U.S. Pat. No. 7,883,734, which is a National Stage (371) of PCT/JP03/13700, filed on Oct. 27, 2003, and claims priority to JP 2002-313080, filed on Oct. 28, 2002, JP 2002-313081, filed on Oct. 28, 2002, JP 2002-339735, filed on Nov. 22, 2002, JP 2002-348796, filed on Nov. 29, 2002, JP 2002-348791, filed on Nov. 29, 2002, and JP 2003-086895, filed on Mar. 27, 2003.

FIELD OF THE INVENTION

This invention relates to a process for selectively removing caffeine from a caffeine-containing catechin composition, and also to a packaged beverage containing a composition obtained by the process.

BACKGROUND OF THE INVENTION

Catechins are known to have inter alia a suppressing effect on an increase in cholesterol level and an inhibitory effect on α-amylase activity (for example, JP-A-60-156614 and JP-A-03-133928). To have such physiological effects of catechins developed, it is necessary for an adult to drink 4 to 5 cups of tea in a day. Accordingly, there is an outstanding desire for technology that permits the addition of catechins at high concentration in beverages to facilitate the ingestion of a large amount of catechins.

In tea leaves, however, caffeine components are also contained generally at from 2 to 4% although catechins are contained as much as about 15%. As caffeine exhibits a central nervous system stimulant effect, it is used for the suppression of sleepiness. On the other hand, its excessive ingestion is said to become a cause of induction of adverse effects such as nervosity, nausea and hyposomnia. Thus investigations have been made about processes that can selectively remove only caffeine from caffeine-containing compositions.

As decaffeination processes of coffee, for example, there have been proposed a process that coffee is brought into contact with a caffeine adsorbent such as activated carbon under from 150 to 250 atm (JP-A-53-18772) and a process that caffeine is selectively removed by bringing a caffeine-containing, aqueous solution into contact with activated clay or acid clay (JP-A-06-142405).

However, the former relates to a supercritical extraction technique, so that it requires substantial investment on process equipment and lacks readiness in its practice on an industrial level. This process also involves a problem in that it achieves not only selective removal of only caffeine but also results in a modification to the composition of catechins as effective ingredients. The latter process, on the other hand, is accompanied by a problem in that the hue may deteriorate in some instances, although caffeine can be selectively removed by simply using activated clay or acid clay.

SUMMARY OF THE INVENTION

An object of the present invention is to provide a process for selectively removing caffeine from a caffeine-containing catechin composition without substantially changing the composition of catechins and moreover, without deteriorating the hue. Another object of the present invention is to provide a packaged beverage containing a decaffeinated, catechin-containing composition obtained as described above.

The present inventors have found that caffeine contained in a catechin composition can be selectively removed without substantially changing the composition of catechins and also deteriorating the hue by bringing the catechin composition, in a state dissolved in a mixed water/organic solvent solution of a specific ratio, into contact with activated carbon alone or with activated carbon and acid clay or activated clay. They have also found that a tea extract obtained as described above is good in hue and stability while containing catechins and is useful as a beverage or as a raw material for beverages.

Therefore, the present invention provides a process for selectively removing caffeine from a caffeine-containing catechin composition, which comprises dissolving the caffeine-containing catechin composition in a 9/1 to 1/9 by weight mixed solution of an organic solvent and water, and then bringing the resultant solution into contact with activated carbon.

The present invention also provides a process for selectively removing caffeine from a caffeine-containing catechin composition, which comprises dissolving the caffeine-containing catechin composition in a 9/1 to 1/9 by weight mixed solution of an organic solvent and water, and then bringing the resultant solution into contact with activated carbon and acid clay or activated clay.

The present invention also provides a process for producing a green tea extract, which comprises dissolving a caffeine-containing catechin composition in a 9/1 to 1/9 by weight mixed solution of an organic solvent and water, and then bringing the resultant solution into contact with activated carbon to selectively remove caffeine.

The present invention further provides a process for producing a green tea extract, which comprises dissolving a caffeine-containing catechin composition in a 9/1 to 1/9 by weight mixed solution of an organic solvent and water, and then bringing the resultant solution into contact with activated carbon and acid clay or activated clay to selectively remove caffeine.

The present invention still further provides a caffeine-containing tea extract, wherein:

(a) a content of gallates in non-polymer catechins is from 45 to 60 wt %, (b) a weight ratio of the non-polymer catechins to caffeine is from 8 to 40, (c) a weight ratio of the non-polymer catechins to (sucrose+glucose) is from 2 to 15, and (d) dietary fibers amount to 0.5 wt % or less of a solid content.

The present invention yet further provides a packaged beverage comprising a green tea extract obtained by one of the above-described processes.

DETAILED DESCRIPTION OF THE INVENTION

A caffeine-containing catechin composition used in the present invention contains one or more non-polymer catechins. The term "non-polymer catechins" as used herein is a generic term, which collectively encompasses non-epicatechins such as catechin, gallocatechin, catechingallate and gallocatechingallate, and epicatechins such as epicatechin, epigallocatechin, epicatechingallate and epigallocatechingallate.

As caffeine-containing catechin compositions containing non-polymer catechins, extracts obtained from tea leaves such as green tea, black tea and oolong tea can be mentioned.

In addition, mixtures of caffeine derived from caffeine-containing plants such as coffee with tea extracts are also usable.

Tea leaves for use in the present invention include, tea leaves prepared from tea leaves of the Genus *Camellia*, for example, *C. sinensis, C. assamica* and the *Yabukita* variety, or their hybrids. Such prepared tea leaves include green teas such as sencha (middle-grade green tea), bancha (coarse green tea), gyokuro (shaded green tea), tencha (powdered tea) and kamairicha (roasted tea).

The extraction of a caffeine-containing catechin composition from tea leaves can be conducted by a method such as stirring extraction. An organic acid or organic acid salt, such as sodium ascorbate, can be added beforehand to water upon extraction. It is also possible to make combined use of boiling deaeration or an extraction method which is conducted while bubbling an inert gas such as nitrogen gas to eliminate dissolved oxygen, that is, under a so-called non-oxidizing atmosphere.

Instead of extracting from tea leaves, it is also possible to use a concentrate of a tea extract or a purified product of a concentrate of a tea extract in a form dissolved in or diluted with water. It is also possible to use an extract from tea leaves in combination with a concentrate of a tea extract or a purified product of a concentrate of a tea extract.

The term "the concentrate of a tea extract" as used herein means one obtained by concentrating an extract of tea leaves in hot water or a water-soluble organic solvent, and includes, for example, those prepared by the processes disclosed in JP-A-59-219384, JP-A-04-20589, JP-A-05-260907, JP-A-05-306279 and the like.

As the concentrate of a tea extract, it is possible to use, specifically a commercially-available crude catechin preparation such as "POLYPHENON" (product of Tokyo Food Techno Co., Ltd.), "TEAFURAN" (product of ITO EN, LTD.) or "SUNPHENON" (product of Taiyo Kagaku Co., Ltd.).

As the caffeine-containing catechin composition used as a raw material, it is preferred to use a green tea extract containing from 25 to 90 wt %, more preferably from 25 to 70 wt %, even more preferably from 25 to 40 wt % of non-polymer catechins in terms of solid content, because taste components other than the non-polymer catechins still remain. The term "solid content" as used herein means the weight of a caffeine-containing catechin composition as determined when the caffeine-containing catechin composition is dried and solidified.

As the purified product of the concentrate of the tea extract, one purified by one of the following processes (1) to (3) is preferred.

(1) A process for purifying a solid concentrate of a tea extract, said solid concentrate containing from 25 to 40 wt % of non-polymer catechins, which comprises adding the solid concentrate to a 10/0 to 8/2 by weight solvent of an organic solvent and water, adding water to the resultant mixture to adjust a weight ratio of the organic solvent to water to from 9/1 to 5/5, removing undissolved solids, and then, distilling off the solvent.

(2) A process for purifying a solid concentrate of a tea extract, said solid concentrate containing from 25 to 40 wt % of non-polymer catechins, which comprises adding the solid concentrate to a 10/0 to 8/2 by weight solvent of an organic solvent and water, adding water to the resultant mixture to adjust a weight ratio of the organic solvent to water to a range of from 9/1 to 5/5, removing solids from the resultant suspension, and then, distilling off the solvent from a remaining liquid phase.

(3) A process for purifying a concentrate of a tea extract, said concentrate containing from 25 to 40 wt % of non-polymer catechins, which comprises dissolving the concentrate in a mixed solvent of water and an organic solvent, adding an organic solvents to the resultant solution to adjust a weight ratio of the organic solvents to water to a range of from 9/1 to 5/5 such that a precipitate is formed, removing solids from the resultant suspension, and then distilling off the organic solvents from a remaining liquid phase.

As the concentrate of the tea extract for use in these purification processes (1) to (3), a commercially-available catechin preparation is preferred.

A description will firstly be made about the purification processes (1) and (2).

In the purification processes (1) and (2), the solid concentrate of the tea extract is firstly added to and suspended in a 10/0 to 8/2 by weight solvent of an organic solvent and water.

Organic solvents usable at this time include ethanol, methanol, acetone, ethyl acetate, and the like. Preferred are hydrophilic organic solvents such as ethanol, methanol and acetone, with ethanol being more preferred in view of the remaining of the organic solvent as the purified product is assumed to be used in foods.

The weight ratio of the organic solvent to water in the solvent to be used is preferably from 10/0 to 8/2 from the viewpoint of the dispersibility of the solid concentrate of the tea extract.

The weight ratio of the concentrate of the tea extract to the solvent can be preferably from 5:95 to 40-60, more preferably from 10:90 to 30:70 from the standpoint of the efficiency of extraction of non-polymer catechins.

Water is then added to the suspension. As a consequence, water-soluble components contained in the concentrate of the tea extract, such as non-polymer catechins, are subjected to solid-liquid extraction from solid to water. The amount of the water to be added to the suspension is such an amount as required to adjust the weight ratio of the organic solvent to water to from 9/1 to 5/5, preferably from 8/2 to 6/4. An organic solvent/water ratio higher than 9/1 leads to a reduction in the efficiency of extraction from the concentrate of the tea extract to water upon conducting the solid-liquid extraction, and therefore, is not preferred. An organic solvent/water ratio lower than 5/5, on the other hand, results in an insufficient taste-improving effect, and therefore, is not preferred. It is to be noted that water is added further even when the weight ratio of the organic solvent to water in the solvent used at the first is from 9/1 to 8/2. By the addition of water, water-soluble components such as non-polymer catechins are subjected to solid-liquid extraction so that a purified product of a concentrate of a tea extract is obtained with good flavor and taste.

As the manner of addition of water, it is preferred to slowly add it dropwise as much as needed over a time of from 10 to 30 minutes or so, and for an improvement in the efficiency of solid-liquid extraction, it is preferred to add it dropwise under stirring. It is still more preferred to include an aging time of from 10 minutes to 40 minutes or so after the completion of the dropwise addition of water.

Upon adding the mixed solvent, adding water or conducting the solid-liquid extraction, the temperature can be from 0 to 60° C., preferably from 10 to 60° C., more preferably from 10 to 40° C. from the standpoint of convenience for the control of the purification step considering that an organic solvent is used.

Solids are then separated from the suspension, and from the remaining liquid phase, the organic solvent is distilled off to afford a purified product as desired. As a solid-liquid separation method, a conventional method, for example, centrifugation, filtration or the like can be used. As a distillation method of the organic solvent from the liquid phase obtained by the separation, reduced-pressure distillation is preferred to avoid a heat load on the purified product as much as possible although any conventional method can be used.

A description will next be made about the purification process (3).

In the purification process (3), the concentrate of the tea extract is firstly dissolved in water or a mixture of water and an organic solvent. Organic solvents usable at this time include ethanol, methanol, acetone, ethyl acetate, and the like. Preferred are hydrophilic organic solvents such as ethanol, methanol and acetone, with ethanol being more preferred in view of the remaining of the organic solvent as the purified product is assumed to be used in beverages.

The solvent for use in the dissolution of the concentrate of the tea extract is the mixture of water and the organic solvent. The weight ratio of water to the organic solvent can be adjusted between 9/1 and 5/5. A ratio smaller than 5/5 leads to a deterioration in the solubility of the concentrate of the tea extract, and hence, to a reduction in the extraction efficiency of the liquid-liquid extraction.

An organic solvent is then gradually added to the solution of the concentrate of the tea extract such that a precipitate of insoluble components is formed in the solution of the concentrate of the tea extract. As the organic solvent for use in this step, the same organic solvent as that used in the above is preferred.

It is necessary to add, to the solution of the concentrate of the tea extract, the organic solvent in an amount sufficient to adjust the weight ratio of the organic solvents to water to a range of from 9/1 to 5/5, preferably from 8/2 to 6/4 from the standpoint of formation of a precipitate of insoluble components. An organic solvents/water ratio greater than 9/1 requires to use the organic solvent in a considerably large amount, and therefore, is not preferred economically. An organic solvents/water ratio smaller than 5/5, on the other hand, leads to a deterioration in the separability of the precipitate by filtration, and therefore, is not preferred.

As the manner of addition of the organic solvent, it is preferred to slowly add it dropwise as much as needed over a time of from 10 to 30 minutes or so, and for an improvement in the efficiency of formation of insoluble components, it is preferred to add it dropwise under stirring. It is still more preferred to include an aging time of from 10 minutes to 40 minutes or so after the completion of the dropwise addition of water.

Upon forming the precipitate of the insoluble components by the addition of the organic solvent to the solution of the concentrate of the tea extract, no particular limitation is imposed on the temperature. Nonetheless, the temperature can be preferably from 0 to 60° C., more preferably from 10 to 60° C., even more preferably from 10 to 40° C. from the standpoint of convenience for the control of the purification step considering that an organic solvent is used.

Solids are then separated from the suspension, and from the remaining liquid phase, the organic solvents are distilled off to afford a purified product as desired. As a solid-liquid separation method, a conventional method, for example, centrifugation, filtration or the like can be used. As a distillation method of the organic solvent from the liquid phase obtained by the separation, reduced-pressure distillation is preferred to avoid a heat load on the purified product as much as possible although any conventional method can be used.

A description will next be made about the process for selectively removing caffeine from the caffeine-containing catechin composition.

Firstly, the caffeine-containing catechin composition is dissolved in a 9/1 to 1/9 mixed solution of an organic solvent and water.

Organic solvents usable at this time include ethanol, methanol, acetone, ethyl acetate, and the like. Among these, preferred are hydrophilic organic solvents such as ethanol, methanol and acetone, with ethanol being more preferred in view of the use of the purified product in foods.

In the present invention, it is necessary to adjust the weight ratio of the organic solvent to water to a range of from 9/1 to 1/9, preferably from 9/1 to 5/5, more preferably from 8/2 to 6/4. A proportion of the organic solvent greater than 9/1 leads to a reduction in the efficiency of extraction of catechins, while a proportion of the organic solvent smaller than 1/9 results in an insufficient taste-improving effect for the decaffeinated product.

No particular limitation is imposed on the method for dissolving the caffeine-containing catechin composition in the mixed solution of the organic solvent and water. The weight ratio of the organic solvent to water can be adjusted to the range of from 9/1 to 1/9 by adding the organic solvent subsequent to the dissolution of the caffeine-containing catechin composition in water. As an alternative, the organic solvent and water can be brought to a similar ratio by gradually adding water subsequent to the suspension of the caffeine-containing catechin composition in the organic solvent. From the standpoint of the efficiency of extraction, however, it is preferred to gradually add the organic solvent subsequent to the dissolution in water. Upon treatment of the caffeine-containing catechin composition, catechins are adsorbed on activated carbon or on activated carbon and also acid clay or activated clay when the treatment is conducted in water alone. As opposed to the treatment in water alone, the existence of the organic solvent makes it possible to avoid such phenomenon.

In the present invention, it is preferred to conduct the treatment by adding from 10 to 40 weight parts, especially from 15 to 30 weight parts of the caffeine-containing catechin composition to 100 weight parts of the mixed solution of the organic solvent and water, because the caffeine-containing catechin composition can be treated efficiently.

As to the time needed to add water or the organic solvent, it is preferred to slowly add it dropwise over a time of from 10 to 30 minutes or so, and for an improvement in the efficiency of extraction of catechins, it is preferred to add it dropwise under stirring. It is still more preferred to include an aging time of from 10 minutes to 120 minutes or so after the completion of the dropwise addition of water.

These treatments can be conducted at from 10 to 60° C., preferably from 10 to 50° C., more preferably from 10 to 40° C.

No particular limitation is imposed on the activated carbon for use in the present invention insofar as it is generally used on an industrial level. Usable examples include commercially-available products such as "ZN-50" (product of Hokuetsu Carbon Industry Co., Ltd.), "KURARAY COAL GLC", "KURARAY COAL PK-D" and "KURARAY COAL PW-D" (products of Kuraray Chemical K.K.), and "SHIROWASHI AW50", "SHIROWASHI A", "SHIROWASHI M" and "SHIROWASHI C" (products of Takeda Pharmaceutical Company Limited).

The pore volume of the activated carbon may be preferably from 0.01 to 0.8 mL/g, more preferably from 0.1 to 0.7 mL/g. Concerning the specific surface area, on the other hand, one having a specific surface area in a range of from 800 to 1,300 $m^2/g$ is preferred, within which the range of from 900 to 1,200 m²/g is more preferred. It is to be noted that these physical values are those obtained by the nitrogen adsorption method.

The activated carbon can be added preferably in a proportion of from 0.5 to 5 weight parts, more preferably in a proportion of from 0.5 to 3 weight parts to 100 weight parts of the mixed solution of the organic solvent and water. The addition of the activated carbon in an excessively small proportion leads to a deterioration in the efficiency of removal of caffeine, while the addition of the activated carbon in an excessively large proportion leads to an increase in the cake resistance in a filtration step. It is, therefore, not preferred to add the activated carbon in a proportion outside the above-described range.

Acid clay and activated clay for use in the present invention both contain, as general chemical components, $SiO_2$, $Al_2O_3$, $Fe_2O_3$, CaO, MgO, etc., and those having $SiO_2/Al_2O_3$ ratios of from 3 to 12 are preferred, within which the ranges of from 4 to 9 are more preferred. Also preferred are those which have compositions containing from 2 to 5 wt % of $Fe_2O_3$, from 0 to 1.5 wt % of CaO and from 1 to 7 wt % of MgO.

Activated clay is obtained by treating naturally-occurring acid clay (montmorillonite clay) with a mineral acid such as sulfuric acid, and is a compound having a porous structure of large specific surface area and adsorbability. Further treatment of acid clay with an acid is known to change its specific surface area such that its decoloring ability is improved and its physical properties are modified.

The specific surface area of acid clay or activated clay may be preferably from 50 to 350 m²/g although it varies depending on the degree or the like of the acid treatment, and its pH (5% suspension) may be preferably from 2.5 to 8, more preferably from 3.6 to 7. Usable examples of acid clay include commercially-available products such as "MIZUKA ACE #600" (product of Mizusawa Chemical Industries, Ltd.).

Acid clay or activated clay can be added preferably in a proportion of from 2.5 to 25 weight parts, more preferably in a proportion of from 2.5 to 15 weight parts to 100 weight parts of the mixed solution of the organic solvent and water. The addition of acid clay or activated clay in an unduly small proportion leads to a deterioration in the efficiency of removal of caffeine, while the addition of acid clay or activated clay in an excessively large proportion leads to an increase in the cake resistance in the filtration step. It is, therefore, not preferred to add acid clay or activated clay in a proportion outside the above-described range.

When activated carbon is used in combination with acid clay or activated clay, the ratio of activated carbon to acid clay or activated clay may preferably be from 1 to 10 of acid clay or activated clay to 1 activated carbon by weight, with activated carbon:acid clay or activated clay=1:1 to 1:6 being more preferred. Upon bringing into contact with the caffeine-containing catechin composition, activated carbon and acid clay or activated clay can be both brought into contact at the same time or can be individually brought into contact one after another (no limitation is imposed on their order).

The treatment of the caffeine-containing catechin composition by its contact with activated carbon or with activated carbon and also acid clay or activated clay can be conducted by any method such as a batchwise treatment method or a continuous treatment method making use of a column. Adopted in general is a method that powdery activated carbon or the like is added, the resulting mixture is stirred to selectively adsorb caffeine, and filtration is conducted to obtain a decaffeinated filtrate or a method that caffeine is selectively adsorbed by continuous treatment through a column packed with granular activated carbon or the like.

After having been brought into contact with activated carbon or with activated carbon and also acid clay or activated clay, the solution with the catechin composition contained therein is subjected to distillation such as reduced-pressure distillation to remove the organic solvent form the system. After the treatment, the catechin composition can be either liquid or solid. To prepare its a solid form, the catechin composition can be formed into powder by a method such as lyophilization or spray drying.

After the decaffeination treatment by the present invention, the catechin composition preferably contains the non-polymer catechins with a composition substantially unchanged from that before the treatment. The yield of the non-polymer catechins in the mixed solution of the organic solvent and water after the treatment may be preferably 70 wt % or higher, more preferably 80 wt % or higher. Accordingly, the content of the non-polymer catechins in the composition after the decaffeination treatment may preferably be from 80 to 95 wt %, more preferably from 85 to 95 wt %, even more preferably from 90 to 95 wt % in terms of solid content.

Concerning the non-polymer catechins in the catechin composition after the decaffeination treatment by the present invention, the ratio of gallocatechins, which consist of epigallocatechingallate, gallocatechingallate, epigallocatechin and gallocatechin, to non-gallocatechins, which consist of epicatechingallate, catechingallate, epicatechin and catechin, can preferably retain the corresponding ratio in natural green tea leaves. In other words, it is preferred from the standpoint of also retaining the composition of natural green tea leaves in the purified product that the total amount of the above-described four gallocatechins always exceeds the total amount of the above-described four non-gallocatechins.

As the concentration of caffeine relative to that of the non-polymer catechins in the catechin composition after the decaffeination treatment by the present invention, the weight ratio (b) of the non-polymer catechins to caffeine may be preferably from 7 to 60, more preferably from 7 to 50, even more preferably from 8 to 40.

In the catechin composition after the decaffeination treatment by the present invention, the content (a) of the gallates, which consist of catechingallate, epicatechingallate, gallocatechingallate and epigallocatechingallate, in the non-polymer catechins may be preferably 45 wt % or greater, more preferably from 45 to 60 wt % from the standpoint of the effectiveness of physiological effects of the non-polymer catechins.

The weight ratio (c) of the non-polymer catechins to (sucrose+glucose) in the catechin composition after the decaffeination treatment may be preferably from 2 to 15, more preferably from 2 to 10, even more preferably from 2 to 8, even more preferably from 3 to 7. A ratio greater than 15 involves a problem in the flavor of the tea extract, while a ratio smaller than 2 is not preferred because the saccharide content becomes too abundant.

From the standpoint of readiness in the migration of the non-polymer catechins, dietary fibers (d) may amount preferably to 0.5 wt % or less, more preferably to from 0 to 0.3 wt % of the solid content of the catechin composition after the decaffeination treatment.

The addition of the catechin composition obtained after the decaffeination treatment makes it possible to obtain a beverage having a high non-polymer catechin concentration and a low caffeine concentration. As the beverage, a packaged beverage is preferred.

The packaged beverage according to the present invention is a beverage with the above-described specific decaffeinated composition added therein. Beverages and the like, to which the specific decaffeinated composition can be added, include green tea, an extracts of tea selected from semi-fermented tea or fermented tea, and non-tea beverages. Among these, preferred is a beverage with the decaffeinated composition added to a tea extract, and preferred is a green tea beverage with the decaffeinated composition added to an extract of green tea. Illustrative of the semi-fermented tea is oolong tea, and illustrative of the fermented tea is black tea. Examples of the non-tea beverage include carbonated beverages as soft drinks, beverages with fruit extract or extracts, juices with vegetable extract or extracts, near waters, sports drinks, and diet drinks.

The packaged beverage according to the present invention contains generally from 0.092 to 0.5 wt %, preferably from 0.1 to 0.4 wt %, more preferably from 0.11 to 0.3 wt %, even more preferably from 0.12 to 0.3 wt % of the non-polymer catechins, which are non-polymers and are in water-dissolved forms. When the content of the non-polymer catechins falls within the above-described range, a Large amount of the non-polymer catechins can be ingested with ease without producing strong bitterness, astringency and sharp puckeriness. The concentration of the non-polymer catechins can be adjusted depending on the amount of the decaffeinated composition to be added.

The content (a) of gallates—which consist of catechingallate, epicatechin gallate, gallocatechin gallate and epigallocatechin gallate—in the non-polymer catechins in the packaged beverage according to the present invention may preferably be 45 wt % or greater, more preferably from 45 to 60 wt % from the standpoint of the effectiveness of the physiological effects of the non-polymer catechins.

As the concentration of caffeine relative to that of the non-polymer catechins in the packaged beverage according to the present invention, the weight ratio (b) of the non-polymer catechins to caffeine may be preferably from 7 to 60, more preferably from 7 to 50, even more preferably from 8 to 40.

The weight ratio (c) of the non-polymer catechins to (sucrose+glucose) in the packaged beverage according to the present invention may be preferably from 2 to 15, more preferably from 2 to 10, even more preferably from 2 to 8, even more preferably from 3 to 7. A ratio greater than 15 involves a problem in the flavor of the tea extract, while a ratio smaller than 2 is not preferred because the saccharide content of the tea extract is too high.

Dietary fibers (d) may amount to 0.5 wt % or less of the solid content of the catechin composition in the packaged beverage according to the present invention after the decaffeination treatment, and from the standpoint of readiness in the absorption of the non-polymer catechins, it is preferred to contain no dietary fibers.

It is preferred to add a bitterness suppressor to the packaged beverage according to the present invention, because its addition renders the packaged beverage more palatable. No particular limitation is imposed on the bitterness suppressor to be used, although cyclodextrins are preferred. Usable examples of the cyclodextrins include $\alpha$-, $\beta$- and $\gamma$-cyclodextrins and branched $\alpha$-, $\beta$- and $\gamma$-cyclodextrins. A cyclodextrin can be contained at from 0.01 to 0.5 wt %, preferably at from 0.01 to 0.3 wt % in the beverage.

From the standpoint of the chemical stability of the non-polymer catechins, the pH of the beverage may be preferably from 2 to 7, more preferably from 3 to 7, even more preferably from 5 to 7, all at 25° C.

For the packaged beverage according to the present invention, it is possible to add, in combination with the ingredients derived from tea, additives—such as antioxidants, flavors, various esters, organic acids, organic acid salts, inorganic acids, inorganic salts, colorants, emulsifiers, preservatives, seasoning agents, sweeteners, sour seasonings, fruit extracts, vegetable extracts, flower honey extracts, pH regulators and quality stabilizers—either singly or in combination as ingredients which can be added in light of the formulation.

Examples of the sweeteners include sugar, glucose, fructose, isomerized syrup, glycyrrhizin, stevia, aspartame, fructooligosaccharide, and galactooligosaccharide. Examples of the sour seasonings include, in addition to fruit juices and the like extracted from natural sources, citric acid, tartaric acid, malic acid, lactic acid, fumaric acid, and phosphoric acid. These sweeteners and sour seasonings may be contained preferably in an amount of from 0.01 to 0.5 wt %, with from 0.01 to 0.3 wt % being more preferred.

Examples of the inorganic acids and inorganic acid salts include phosphoric acid, disodium phosphate, sodium metaphosphate, and sodium polyphosphate. These inorganic acids and inorganic acid salts may be contained in an amount of from 0.01 to 0.5 wt %, with from 0.01 to 0.3 wt % being preferred, in the beverage.

Similar to general beverages, a container useful for the packaged beverage according to the present invention can be provided in an ordinary form such as a molded container made of polyethylene terephthalate as a principal component (so-called PET bottle), a metal can, a paper container combined with metal foils or plastic films, or a bottle. The term "packaged beverage" as used herein means a beverage which can be drunken without dilution.

The packaged beverage according to the present invention can be produced, for example, by filling the beverage in a container such as a metal can and, when heat sterilization is feasible, conducting heat sterilization under sterilization conditions as prescribed in the Food Sanitation Act. For those which cannot be subjected to retort sterilization like PET bottles or paper containers, a process is adopted such that the beverage is sterilized beforehand under similar sterilization conditions as those described above, for example, by a plate-type heat exchanger, is cooled to a particular temperature, and is then filed in a container. Under aseptic conditions, additional ingredients may be added to and filled in a filled container. It is also possible to conduct an operation such that subsequent to heat sterilization under acidic conditions, the pH of the beverage is adjusted to return to neutral under aseptic conditions or that subsequent to heat sterilization under neutral conditions, the pH of the beverage is adjusted to return to the acidic side under aseptic conditions.

In the present invention, the purified product obtained by any one of the purification processes (1) to (3) contains non-polymer catechins at high concentration and has an improvement in astringency and bitterness, and further, beverages with the purified product added therein have been found to be good in flavor and taste. The present invention, therefore, provides the purification processes (1) to (3) and packaged beverages containing purified products obtained by any one of the purification processes (1) to (3).

The concentration of non-polymer catechins in each purified product according to the present invention can be preferably from 26 to 55 wt %, more preferably from 30 to 55 wt %, even more from 30 to 55 wt %, even more preferably from 35 to 55 wt %.

If the concentration of non-polymer catechins in a purified product is lower than 25 wt %, the effects of other taste components contained in the purified product of the green tea extract come to the fore so that a high non-polymer catechins beverage with the purified product added therein gives a feeling of disagreeable bitterness without any refreshing sensation. Therefore, such a low concentration of non-polymer catechins is not preferred. If the concentration of non-polymer catechins in a purified product is higher than 55 wt %, on the other hand, dainty components other than the non-polymer catechins in the purified product as a catechin preparation have been excessively removed together with oxalic acid. Such a purified product is, therefore, not preferred as a purified product to be added as a catechin preparation to beverages.

It is preferred that the ratio of the gallates—which consist of epigallocatechin gallate, gallocatechin gallate, epigallocatechin and gallocatechin—to the nongallates—which consist of epicatechin gallate, catechingallate, epicatechin and catechin—in the purified product according to the present invention retain the same ratio as in natural green tea leaves. From the standpoint of also retaining the catechin composition of natural green tea leaves in the purified product, it is, therefore, preferred that the total amount of the four types of gallates be always greater than the total amount of the four types of nongallates.

The content of the gallates—which consist of catechingallate, epicatechin gallate, gallocatechin gallate and epigallocatechin gallate—in the purified product according to the present invention may preferably be 45 wt % or greater from the standpoint of the effectiveness of the physiological effects of the non-polymer catechins.

In each purified product obtained by any one of the purification processes according to the present invention, the content weight ratio [(B)/(A)] of (B) oxalic acid to the non-polymer catechins (A) may be preferably from 0.002 to 0.035, more preferably from 0.002 to 0.03, even more preferably from 0.0025 to 0.03, even more preferably from 0.0025 to 0.02. An unduly small content of oxalic acid in a purified product means excessive removal of dainty components and the like together with oxalic acid, so that such a purified product is not preferred as a purified product to be added to beverages. An excessively high content of oxalic acid in a purified product, on the other hand, results in a beverage, which gives a feeling of disagreeable bitterness without any refreshing sensation as felt from the concentrate before the purification. Therefore, such an excessively high content is not preferred.

The concentration of oxalic acid in a purified product according to the present invention may be preferably from 0.05 to 1.5 wt %, more preferably from 0.05 to 1.0 wt %, even more preferably from 0.05 to 0.5 wt %, even more preferably from 0.08 to 0.3 wt %. If the concentration of oxalic acid in the purified product is higher than 1.5 wt %, the oxalic acid component contained in the purified product substantially affects the taste so that a high non-polymer catechins beverage with the purified product added therein gives a feeling of sharp bitterness without any refreshing sensation. Therefore, such a high concentration of oxalic acid is not preferred. If the concentration of oxalic acid in a purified product is lower than 0.05 wt %, on the other hand, dainty components other than the non-polymer catechins in the purified product have been excessively removed together with oxalic acid. Such a purified product is, therefore, not preferred as a purified product to be added to beverages.

The use of a green tea extract in the form of a purified product in which the content weight ratio [(A)/(C)] of (A) non-polymer catechins to (C) total polyphenols has been adjusted to 0.83 to 0.96 provides a packaged beverage the color tone of which remains good even after storage.

The content weight ratio [(A)/(C)] of (A) the non-polymer catechins to (C) the total polyphenols in the green tea extract can be from 0.83 to 0.96, preferably from 0.83 to 0.94, more preferably from 0.84 to 0.93, even more preferably from 0.84 to 0.92. An excessively low ratio of non-polymer catechins to total phenols in a green tea extract results in the abundant inclusion of components other than the non-polymer catechins in a beverage, thereby impairing the stability of the color tone of the beverage during its storage. Therefore, such an excessively low ratio is not preferred. An unduly high ratio of non-polymer catechins to total phenols in a green tea extract leads to a change to the balance of flavor and taste of the beverage. Therefore, such an excessively high ratio is not preferred either.

The term "total polyphenols" as used herein means ingredients quantitated by the method that by using ethyl gallate as a standard solution, their total amount is determined as an amount converted to gallic acid by the ferrous tartrate method (referential publication: "Green Tea Polyphenols" (in Japanese), Technology Series for the Effective Utilization of Functional Ingredients for Beverages and Foods, No. 10). In general, non-polymer catechins and their polymers and the like can be detected by this measurement method.

It is preferred that the ratio of the gallates—which consist of epigallocatechin gallate, gallocatechin gallate, epigallocatechinandgallocatechin—to the nongallates—which consist of epicatechin gallate, catechingallate, epicatechin and catechin—in the green tea extract retain the same ratio as in natural green tea leaves. Accordingly, the purification should be conducted under such conditions that the total amount of the four types of gallates is always greater than the total amount of the four types of nongallates.

The content of the gallates—which consist of catechingallate, epicatechin gallate, gallocatechin gallate and epigallocatechin gallate—in the green tea extract may preferably be 45 wt % or greater from the standpoint of the effectiveness of the physiological effects of the non-polymer catechins.

The concentration of (C) total polyphenols in the green tea extract may be preferably from 35 to 60 wt %, more preferably from 35 to 55 wt %, even more preferably from 40 to 55 wt %. If the concentration of total polyphenols in a green tea extract is higher than 60 wt %, the content of other taste components contained in the green tea extract is low so that the green tea extract may be disturbed in the balance of its flavor and taste. If the concentration of total polyphenols in a green tea extract is lower than 35 wt %, on the other hand, the concentration of non-polymer catechins as an effective ingredient is low so that the green tea extract has to be added in a greater amount to a beverage.

A packaged beverage with the green tea extract added therein can be a tea-based beverage or non-tea-based beverage like the above-described packaged beverage. The concentration of non-polymer catechins in the packaged beverage can be from 0.092 to 0.5 wt % as in the above-described packaged beverage. Further, the content of epicatechins and that of gallates can preferably be similar to their contents in the above-described packaged beverage. In addition, a bitterness suppressor, a sweetener and other ingredients can also be added to the packaged beverage, and the pH of the packaged beverage can be preferably from 2 to 7, more preferably from 3 to 7, even more preferably from 5 to 7, all at 25° C.

Examples

Measurement of Catechins

A catechin composition was diluted with distilled water. Subsequent to filtration through a filter (0.8 μm), the filtrate was subjected to chromatography at a column temperature of 35° C. by a gradient elution method, which used Solution A and Solution B, while employing a high-performance liquid chromatograph (model: "SCL-10AVP") manufactured by Shimadzu Corporation and fitted with an LC column packed with octadecyl-introduced silica gel, "L-Column, TM ODS" (4.6 mm in diameter×250 mm in length; product of Chemicals Evaluation and Research Institute, Japan). A 0.1 mol/L solution of acetic acid in distilled water and a 0.1 mol/L solution of acetic acid in acetonitrile were used Solution A and Solution B, respectively. The measurement was conducted under the conditions of 20 µL injected sample quantity and 280 nm UV detector wavelength.

Measurement of Caffeine (Analyzer)

A high-performance liquid chromatograph (manufactured by Hitachi, Ltd.) was used.

Plotter: "D-2500", Detector: "L-4200", Pump: "L-7100",
Autosampler: "L-7200", Column: "Inertsil ODS-2" (2.1 mm inner diameter×250 mm length).

(Analysis Conditions)

Injected sample quantity: 10 µL
Flow rate: 1.0 mL/min
Detection wavelength of UV spectrophotometer: 280 nm
Eluent A: 0.1 M solution of acetic acid in water
Eluent B: 0.1 M solution of acetic acid in acetonitrile
Concentration gradient conditions (vol. %)

| Time | Eluent A | Eluent B |
|---|---|---|
| 0 min | 97% | 3% |
| 5 min | 97% | 3% |
| 37 min | 80% | 20% |
| 43 min | 80% | 20% |
| 43.5 min | 0% | 100% |
| 48.5 min | 0% | 100% |
| 49 min | 97% | 3% |
| 62 min | 97% | 3% |

(Retention time of caffeine)
Caffeine: 27.2 min

From each area % determined here, the corresponding wt % was determined based on the standard substance.

Measurement of Oxalic Acid

An ion chromatograph (model: "DXAQ 1110"; manufactured by Japan Dionex Co., Ltd.) was fitted with columns ("IonPac AS4A-SC", 4×250 mm column), and was connected to a suppressor, "ASRS-ULTRA" (manufactured by Dionex Corporation). Measurement of oxalic acid was performed in the recycle mode. As mobile phases, a 1.8 mmol/L $Na_2CO_3$ aqueous solution and 1.7 mmol/L $NaHCO_3$ aqueous solution were fed at 1.0 mL/min. The injected sample quantity was set at 25 µL. An electrical conductivity detector was used as a detector.

Measurement of Total Polyphenols

Using ethyl gallate as a standard solution, total polyphenols were determined as an amount converted to gallic acid by the ferrous tartrate method (referential publication: "Green Tea Polyphenols" (in Japanese), Technology Series for the Effective Utilization of Functional Ingredients for Beverages and Foods, No. 10). A sample (5 mL) was stained with the standard ferrous tartrate solution (5 mL). With a phosphate buffer, the volume of the thus-stained sample was adjusted to 25 mL. Its absorbance was measured at 540 nm, and from a calibration line for ethyl gallate, the amount of total polyphenols was determined.

Preparation of the standard ferrous tartrate solution: Ferrous sulfate heptahydrate (100 mg) and potassium sodium tartrate (Rochelle salt, 500 mg) were dissolved with distilled water to 100 mL.

Preparation of the phosphate buffer: A 1/15 M solution of disodium hydrogenphosphate and a 1/15 M solution of sodium dihydrogenphosphate were mixed to give pH 7.5.

Ranking of Hue (Absorbance)

(Analyzer)

An analyzer, "UV MINI1240" (manufactured by Shimadzu Corporation) was used.

Absorbance values were measured at 450 nm by a spectrophotometer. In each measurement, the catechin composition after its purification was diluted with deionized water such that the concentration of catechins was adjusted to 100 mg %. Using a sample of the diluted composition, its absorbance was measured, and the absorbance was employed as an index for hue.

Visual Ranking of Stability

Each catechin composition after its purification was diluted with deionized water such that the concentration of catechins was adjusted to 100 mg %. A sample for ranking, which had been placed in a 50-mL vial, was observed for the conditions of its contents on an illuminator to visually determine its stability.

Example 1 & Comparative Examples 1-2

Under the conditions shown in Table 1, a caffeine-containing catechin composition was treated to remove caffeine.

It is to be noted that in the employed caffeine-containing catechin composition ("POLYPHENONE HG", product of Tokyo Food Techno Co., Ltd.), the content of non-polymer catechins: 33.70 wt %, the content of caffeine: 5.5 wt %, non-polymer catechins/caffeine=6.1, and the content of gallates: 50.7 wt %.

Treatment Processes (1) Example 1

The caffeine-containing catechin composition ("POLYPHENONE HG", product of Tokyo Food Techno Co., Ltd.; 100 g) was suspended in a 95% aqueous solution of ethanol (490.9 g) at room temperature under stirring at 250 rpm, and subsequent to the addition of activated carbon ("KURARAY COAL GLC", product of Kuraray Chemical K.K.; 20 g), stirring was continued for about 10 minutes. After a 40% aqueous solution of ethanol (409.1 g) was added dropwise over 10 minutes, stirring was continued for about 30 minutes still at room temperature. The activated carbon and a precipitate were filtered off through No. 2 filter paper, followed by the re-filtration through a 0.2-µm membrane filter. Finally, deionized water (200 g) was added to the filtrate, and ethanol was distilled off at 40° C. and 25 Torr to afford a product.

(2) Comparative Example 1

Treatment was conducted in a similar manner as in Example 1 except that the activated carbon was not added.

(3) Comparative Example 2

The caffeine-containing catechin composition ("POLYPHENONE HG", product of Tokyo Food Techno Co., Ltd.; 100 g) was suspended in water (900 g) at room temperature under stirring at 250 rpm, and subsequent to the addition of activated carbon ("KURARAY COAL GLC", product of Kuraray Chemical K.K.; 20 g), stirring was continued for about 20 minutes. Subsequently, stirring was continued for about 30 minutes still at room temperature. Subsequent to filtration through No. 2 filter paper, re-filtration was conducted through a 0.2-μm membrane filter. Finally, until the water content was reduced to a similar level as in Example 1, water was caused to gradually evaporate in a drier to afford a product.

Mizusawa Chemical Industries, Ltd.; 100 g), stirring was continued for about 10 minutes. After a 40% aqueous solution of ethanol (409.1 g) was added dropwise over 10 minutes, stirring was continued for about 30 minutes still at room temperature. The activated carbon and a precipitate were filtered off through No. 2 filter paper, followed by the re-

TABLE 1

|  | Example 1 | Comp. Ex. 1 | Comp. Ex. 2 |
|---|---|---|---|
| Caffeine-containing catechin composition (g) ("POLYPHENONE HG", product to Tokyo Food Techno Co., Ltd) | 100 | 100 | 100 |
| Ethanol (g) | 630 | 630 | 0 |
| Water (g) | 270 | 270 | 900 |
| Activated carbon (g) ("KURARAY COAL GLC", product of Kuraray Chemical K.K.) | 20 | 0 | 20 |
| Organic solvent/water (weight ratio) | 70/30 | 70/30 | 0/100 |
| Amounts of catechins after removal of ethanol[1] (wt %) |  |  |  |
| GC (gallocatechin) | 6.78 | 6.06 | 7.27 |
| EGC (epigallocatechin) | 31.6 | 34.0 | 34.2 |
| C (catechin) | 2.10 | 1.92 | 0.98 |
| EC (epicatechin) | 9.04 | 9.22 | 8.77 |
| EGCg (epigallocatechin gallate) | 37.7 | 36.1 | 36.4 |
| GCg (gallocatechin gallate) | 1.47 | 0.88 | 1.50 |
| ECg (epicatechin gallate) | 10.6 | 11.0 | 10.2 |
| Cg (catechin gallate) | 0.68 | 0.88 | 0.75 |
| Amount of catechins after purification/ amount of catechins before purification | 1.037 | 1.057 | 0.955 |
| Concentration of caffeine after purification[2] (mg %) | 17.8 | 30.0 | 18.6 |
| Amount of caffeine after purification/ Amount of caffeine before purification [—] | 0.591 | 1.00 | 0.955 |
| Non-polymer catechins after purification/ caffeine after purification [—] | 10.7 | 6.4 | 9.4 |
| Content of gallates in non-polymer catechins after treatment (wt. %) | 50.3 | 49.1 | 48.0 |
| Absorbance(—) | 0.052 | 0.107 | 0.163 |
| Evaluation of purified product | Taste was good, and the hue of the purified product was also good. | Caffeine was not removed. | The hue of the purified product was deteriorated although no problem arose in taste. |

[2]Composition of non-polymer catechins in "POLYPHENONE HG" preparation: GC (gallocatechin): 6.39%, EGC (epigallocatechin): 29.42%, C (catechin): 2.16%, EC (epicatechin): 10.3%, EGCg (epigallocatechin gallate): 37.13%, GCg (gallocatechin gallate): 1.93%, ECg (epicatechin gallate): 11.89%, Cg (catechin gallate): 0.79%; content of gallates: 51.73%, content of gallocatechins: 74.88%.
[2]Amount of caffeine in the aqueous solution of "POLYPHENONE HG" = 30.1 mg/100 g = 30.1 mg % (Concentration of caffeine based on the water content after purification).

As evident from the results in Table 1, the treatment of a caffeine-containing catechin composition by the present invention makes it possible to selectively remove caffeine while retaining the composition of catechins, and to obtain a catechin composition with an improved hue.

Examples 2-3 & Comparative Examples 3-4

Under the conditions shown in Table 2, a caffeine-containing catechin composition was treated to remove caffeine.

It is to be noted that in the employed caffeine-containing catechin composition ("POLYPHENONE HG", product of Tokyo Food Techno Co., Ltd.), the content of non-polymer catechins: 33.70 wt %, the content of caffeine: 5.5 wt %, non-polymer catechins/caffeine=6.1, and the content of gallates: 50.7 wt %.

(Treatment Process of Example 2)

The caffeine-containing catechin composition ("POLYPHENONE HG", product of Tokyo Food Techno Co., Ltd.; 100 g) was suspended in a 95% aqueous solution of ethanol (490.9 g) at room temperature under stirring at 250 rpm, and subsequent to the addition of activated carbon ("KURARAY COAL GLC", product of Kuraray Chemical K.K.; 20 g) and acid clay ("MIZUKA ACE #600", product of filtration through a 0.2-μm membrane filter. Finally, deionized water (200 g) was added to the filtrate, and ethanol was distilled off at 40° C. and 25 Torr to afford a product.

(Treatment Process of Example 3)

The caffeine-containing catechin composition ("POLYPHENONE HG", product of Tokyo Food Techno Co., Ltd.; 300 g) was suspended in a 47.5% aqueous solution of ethanol (630 g) at room temperature under stirring at 250 rpm, and subsequent to dissolution for 20 minutes, a 95% aqueous solution of ethanol (570 g) was added dropwise over 20 minutes. After acid clay ("MIZUKA ACE #600", product of Mizusawa Chemical Industries, Ltd.; 30 g) was added, stirring was continued for 2 hours. The activated carbon and a precipitate were then filtered off through No. 2 filter paper. Activated carbon ("KURARAY COAL GLC", product of Kuraray Chemical K.K.; 30 g) was then added to the filtrate, followed by stirring for 2 hours. Subsequently, the activated carbon was filtered off through No. 2 filter paper, and re-filtration was conducted through a 0.2-μm membrane filter. Finally, deionized water (230 g) was added to the filtrate, and ethanol was distilled off at 40° C. and 25 Torr to afford a product.

(Treatment Process of Comparative Example 3)

The caffeine-containing catechin composition ("POLYPHENONE HG", product of Tokyo Food Techno Co., Ltd.; 100 g) was suspended in water (900 g) at room temperature under stirring at 250 rpm, and subsequent to the addition of acid clay ("MIZUKA ACE #600", product of Mizusawa Chemical Industries, Ltd.; 100 g), stirring was continued for about 20 minutes. Subsequently, stirring was continued for about 30 minutes still at room temperature. Subsequent to filtration through No. 2 filter paper, re-filtration was conducted through a 0.2-μm membrane filter. Finally, until the water content was reduced to a similar level as in Example 2, water was gradually evaporated in a drier to of ford a product.

(Treatment Process of Comparative Example 4)

The caffeine-containing catechin composition ("POLYPHENONE HG", product of Tokyo Food Techno Co., Ltd.; 100 g) was suspended in water (900 g) at room temperature under stirring at 250 rpm, and subsequent to the addition of activated carbon ("KURARAY COAL GLC", product of Kuraray Chemical K.K.; 20 g) and acid clay ("MIZUKA ACE #600", product of Mizusawa Chemical Industries, Ltd.; 100 g), stirring was continued for about 20 minutes. Subsequently, stirring was continued for about 30 minutes still at room temperature. Subsequent to filtration through No. 2 filter paper, re-filtration was conducted through a 0.2-μm membrane filter. Finally, until the water content was reduced to a similar level as in Example 2, water was gradually evaporated in a drier to afford a product.

As evident from the results in Table 2, the treatment of a caffeine-containing catechin composition by the present invention makes it possible to selectively remove caffeine while retaining the composition of catechins, and to obtain a catechin composition with an improved hue.

Example 4

The caffeine-containing catechin composition ("POLYPHENONE HG", product of Tokyo Food Techno Co., Ltd.; the content of non-polymer catechins: 33.70 wt %, the content of caffeine: 5.5 wt %, non-polymer catechins/caffeine: 6.1, the content of gallates: 50.7 wt %; 12.8 kg) was dissolved in deionized water (13.44 kg). 95% ethanol (13.44 kg) was then added, followed by mixing and stirring. Similarly, 95% ethanol was then added at a dropping rate of 22 kg/hr to conduct extraction. Subsequent to the extraction for 30 minutes, acid clay (2 kg) was added to the resultant extract (64 kg) to conduct a clay treatment. After the clay treatment, solid-liquid separation was conducted by filtration. To the clay-treated filtrate obtained as described above, activated carbon (1 kg) was added to conduct an activated carbon treatment. After the activated carbon treatment, filtration was applied to collect a filtrate. The thus-obtained filtrate was concentrated to remove ethanol, and the solid concentration was adjusted with deionized water to afford a desired product.

TABLE 2

| | Example 2 | Example 3 | Comp. Ex. 3 | Comp. Ex. 4 |
|---|---|---|---|---|
| Caffeine-containing catechin composition (g) ("POLYPHENONE HG", product to Tokyo Food Techno Co., Ltd) | 100 | 300 | 100 | 100 |
| Ethanol (g) | 630 | 825.8 | 0 | 0 |
| Water (g) | 270 | 374.2 | 900 | 900 |
| Activated carbon (g) ("KURARAY COAL GLC", product of Kuraray Chemical K.K.) | 20 | 30 | 0 | 20 |
| Acid clay (g) ("MIZUKA ACE #600", product of Mizusawa Chemical Industries, Ltd.) | 100 | 30 | 100 | 100 |
| Organic solvent/water (weight ratio) | 70/30 | 71/29 | 0/100 | 0/100 |
| Amounts of non-polymer catechins after treatment (wt %)[1] | | | | |
| GC (gallocatechin) | 6.81 | 7.21 | 6.75 | 7.42 |
| EGC (epigallocatechin) | 32.08 | 29.74 | 31.75 | 34.72 |
| C (catechin) | 2.09 | 1.36 | 0.22 | 2.02 |
| EC (epicatechin) | 8.96 | 9.38 | 9.64 | 8.24 |
| EGCg (epigallocatechin gallate) | 37.12 | 37.76 | 35.93 | 35.86 |
| GCg (gallocatechin gallate) | 1.39 | 1.80 | 1.39 | 1.47 |
| ECg (epicatechin gallate) | 10.78 | 11.31 | 11.34 | 9.61 |
| Cg (catechin gallate) | 0.75 | 0.45 | 0.94 | 0.66 |
| Non-polymer catechins/caffeine after treatment (weight ratio) | 38.8 | 8.8 | 23.6 | 42.6 |
| Amount of caffeine after treatment[2] (mg/100 mL) | 4.8 | 18.1 | 8.2 | 4.3 |
| Content of gallates in non-polymer catechins after treatment (wt %) | 50.0 | 51.3 | 49.6 | 47.6 |
| Content of gallocatechins in non-polymer catechins after treatment (wt %) | 77.4 | 76.5 | 75.8 | 79.5 |
| Absorbance(—) | 0.044 | 0.073 | 0.535 | 0.270 |
| Evaluation of purified product | Caffeine was decreased, and hue and stability were both good. | Caffeine was decreased, and hue and stability were both good. | Hue was deteriorated, and a precipitate occurred | Hue was deteriorated, and a precipitate occurred |

[1] Composition of non-polymer catechins in "POLYPHENONE HG" preparation: GC (gallocatechin): 6.39%, EGC (epigallocatechin): 29.42%, C (catechin): 2.16%, EC (epicatechin): 10.3%, EGCg (epigallocatechin gallate): 37.13%, GCg (gallocatechin gallate): 1.93%, ECg (epicatechin gallate): 11.89%, Cg (catechin gallate): 0.79%; content of gallates: 51.73%, content of gallocatechins: 74.88%.
[2] Amount of caffeine when "POLYPHENONE HG" was dissolved in water: 30.1 mg/100 g.

TABLE 3

Analysis Data of Caffeine-containing Tea Extract

| | | |
|---|---|---|
| Content of gallates in non-polymer catechins | wt % | 53.68 |
| Non-polymer catechins/caffeine | — | 10.31 |
| Non-polymer catechins/(sucrose + glucose) | — | 4.76 |
| Dietary fibers in product in terms of solid content | wt % | 0.50 |
| Absorbance | — | 0.082 |

* The data of sucrose, glucose (the HPLC method) and dietary fibers (the enzymatic gravimetric method) are the analysis data disclosed by Japan Food Research Laboratories (described in the May 2000 edition of "Table of Fees on Primary Items for Analysis" (in Japanese), Japan Food Research Laboratories).

Examples 5-7

Using the purified products of the green tea extract as obtained in Examples 1 to 3, the packaged beverages shown in Table 4 were produced.

TABLE 4

| | | Examples | | |
|---|---|---|---|---|
| | | 5 | 6 | 7 |
| Purified product[1] of green tea extract | (g) | 5.25 | | |
| Purified product[2] of green tea extract | (g) | | 5.36 | |
| Purified product[3] of green tea extract | (g) | | | 6.27 |
| β-cyclodextrin | (g) | 2.8 | 2.8 | 2.8 |
| Sodium ascorbate | (g) | 1.0 | 1.0 | 1.0 |
| Sodium bicarbonate | (g) | q.s. | q.s. | q.s. |
| Commercially-available drinking water[4] | (g) | Balance | Balance | Balance |
| Total weight | (g) | 1,000 | 1,000 | 1,000 |
| pH | | 6.2 | 6.2 | 6.2 |
| Post-treatment temperature | (° C.) | 139 | 139 | 139 |
| Post-treatment time | (min) | 8 | 8 | 8 |
| Total amount of non-polymer catechins in beverage | wt % | 0.1 | 0.1 | 0.1 |
| Amount of caffeine in beverage | wt % | 0.0093 | 0.0026 | 0.012 |
| Content of gallates in non-polymer catechins in beverage | wt % | 50.3 | 50.0 | 51.3 |
| Non-polymer catechins/caffeine in beverage | [—] | 10.7 | 38.8 | 8.8 |
| Color tone stability of beverage[5] | | Good | Very good | Good |

[1] Purified product of green tea extract as obtained in Example 1.
[2] Purified product of green tea extract as obtained in Example 2.
[3] Purified product of green tea extract as obtained in Example 3.
[4] Commercially-available drinking water. Quality marking - calcium content: 7.1 mg/100 mL, magnesium content: 2.4 mg/100 mL, sodium content: 4.7 mg/100 mL.
[5] Each packaged beverage which had been subjected to a post-treatment was left over at 55° C. for 1 week, during which the packaged beverage was observed for any change in appearance.

Examples 8-11 & Comparative Examples 5-6

Purification of the commercially-available catechin preparation was conducted by solid-liquid extraction under varied organic solvent/water ratios as shown in Table 5. Specifically, ethanol or acetone was used as an organic solvent, and the catechin preparation was added to a mixed solvent of the organic solvent and water. After water was added to give the corresponding organic solvent/water ratio shown in Table 5, the resulting mixture was stirred and then filtered to remove solids. Further, the organic solvent was distilled off under reduced pressure.

TABLE 5

| | | Example 8 | Example 9 | Example 10 | Example 11 | Comp. Ex. 5 | Comp. Ex. 6 |
|---|---|---|---|---|---|---|---|
| Amount of "POLYPHENONE HG"[2] to be suspended | g | 10 | 10 | 10 | 10 | 10 | 10 |
| Amount of ethanol upon suspension | g | 100 | | 80 | 95 | 60 | 100 |
| Amount of acetone upon suspension | g | | 100 | | | | |
| Amount of water upon suspension | g | | | 20 | 5 | 40 | |
| Total amount upon suspension | g | 110 | 110 | 110 | 110 | 110 | 110 |
| Amount of water added for solid-liquid extraction | g | 42.9 | 42.9 | 60 | 5.6 | 20 | 150 |
| Organic solvent/water ratio upon solid-liquid extraction | — | 70/30 | 70/30 | 50/50 | 90/10 | 50/50 | 40/60 |
| Oxalic acid/non-polymer catechins ratio after purification | | 0.011 | 0.005 | 0.031 | 0.007 | 0.037 | 0.060 |
| Concentration of non-polymer catechins in solids after purification | wt % | 37 | 37 | 34 | 42 | 34 | — |
| Content of gallates in non-polymer catechins contained in solids after purification | wt % | 55.36 | 54.71 | 55.64 | 53.77 | 51.17 | — |

TABLE 5-continued

|  | Example 8 | Example 9 | Example 10 | Example 11 | Comp. Ex. 5 | Comp. Ex. 6 |
|---|---|---|---|---|---|---|
| Evaluation of flavor and taste of 0.1 wt % dissolution system of non-polymer catechins | No problem | No problem | Slight acid taste was felt. | No problem | Acid taste was felt. | Acid taste was strong. |

1) Each catechin preparation after its purification was added to deionized water such that the concentration of non-polymer catechins was adjusted to 0.1 wt %. Evaluation was performed by three taste panelists.
2) Concentrate of a green tea extract "POLYPHENONE HG" (product of Tokyo Food Techno Co., Ltd.) The content of non-polymer catechins: 33.70 wt %, the content of oxalic acid: 2.03 wt %, oxalic acid/non-polymer catechins: 0.060

It has been found that by adjusting the ratio of oxalic acid to non-polymer catechins to 0.01 or so as a result of purification, the effects of taste components existing in a catechin preparation become no longer sensible to give good results from the standpoint of flavor and taste. It has also been found that, when the ratio of an organic solvent to water is set at 5/5 upon conducting solid-liquid extraction, a difference arises in the taste of a purified product depending upon the ratio of an organic solvent to water upon suspension.

Examples 12-15 & Comparative Example 7

By changing the ratio of an organic solvent to water upon liquid-liquid extraction as shown in Table 6 to adjust the amount of insoluble components to be formed, purification of the commercially-available catechin preparation was conducted. Specifically, the commercially-available catechin preparation was dissolved in a mixed solvent of water and ethanol, and then, ethanol was added to adjust the ethanol/water ratio to the corresponding ratio described in Table 1 such that a precipitate was caused to occur. Solids were filtered off, and then, ethanol was distilled off under reduced pressure.

It has been found that by setting the ethanol/water ratio at 70/30 upon liquid-liquid extraction, the ratio of oxalic acid to non-polymer catechins becomes extremely low after purification and the acid taste of conventional catechins becomes no longer sensible. It has also been found that the efficiency of purification becomes higher by dissolving a catechin preparation in an aqueous ethanol solution rather than in 100% water upon dissolution of the catechin preparation.

Examples 16-17 & Comparative Example 8-9

Packaged beverages were each produced by mixing its corresponding ingredients and conducting its corresponding post-treatment as shown in Table 7.

TABLE 6

|  |  | Example 12 | Example 13 | Example 14 | Example 15 | Comp. Ex. 7 |
|---|---|---|---|---|---|---|
| Amount of "POLYPHENONE HG"[2] to be dissolved | g | 10 | 10 | 10 | 10 | 10 |
| Amount of ethanol upon dissolution | g | 60 | 40 | 30 | 50 | 0 |
| Amount of water upon dissolution | g | 40 | 60 | 70 | 50 | 100 |
| Total amount upon dissolution | g | 100 | 100 | 100 | 100 | 100 |
| Amount of ethanol added for liquid-liquid extraction | g | 33.3 | 100 | 133.3 | 150.0 | 233.3 |
| Organic solvent/water ratio upon liquid-liquid extraction | — | 70/30 | 70/30 | 70/30 | 80/20 | 70/30 |
| Oxalic acid/non-polymer catechins ratio after purification | — | 0.0016 | 0.0022 | 0.0025 | 0.0014 | 0.0377 |
| Concentration of non-polymer catechins in solids after purification | wt % | 37 | 37 | 37 | 39 | 37 |
| Content of gallates in non-polymer catechins contained in solids after purification | wt % | 56.77 | 56.65 | 56.14 | 56.80 | 56.26 |
| Evaluation of flavor and taste of 0.1 wt % dissolution system of non-polymer catechins |  | No problem | No problem | No problem | No problem | Acid taste was felt. |

1) Each catechin preparation after its purification was added to deionized water such that the concentration of non-polymer catechins was adjusted to 0.1 wt %. Evaluation was performed by three taste panelists.
2) Concentrate of a green tea extract "POLYPHENONE HG" (product of Tokyo Food Techno Co., Ltd.) The content of non-polymer catechins: 33.70 wt %, the content of oxalic acid: 2.03 wt %, oxalic acid/non-polymer catechins: 0.060

TABLE 7

|  |  | Examples | | Comparative Examples | |
|---|---|---|---|---|---|
|  |  | 16 | 17 | 8 | 9 |
| Green tea extract[1] | (g) | 3.13 | | | |
| Green tea extract[2] | (g) | | 3.10 | | |
| Concentrate[3] of green tea extract | (g) | | | 0.5 | 3.5 |
| Ratio of non-polymer catechins to total polyphenols in the preparation (note) | (—) | 0.85 | 0.91 | 0.81 | 0.81 |
| Dried product[4] of green tea extract | (g) | 1.0 | 1.0 | 1.0 | 1.0 |
| β-Cyclodextrin | (g) | 2.8 | 2.8 | 2.8 | 2.8 |
| Sodium ascorbate | (g) | 1.0 | 1.0 | 1.0 | 1.0 |
| Sodium bicarbonate | (g) | q.s. | q.s. | q.s. | q.s. |
| Commercially-available drinking water[5] | (g) | Balance | Balance | Balance | Balance |
| Total weight | (g) | 1,000 | 1,000 | 1,000 | 1,000 |
| pH |  | 6.2 | 6.2 | 6.2 | 6.2 |
| Post-treatment temperature | (° C.) | 139 | 139 | 139 | 139 |
| Post-treatment time | (min) | 8 | 8 | 8 | 8 |
| Total amount of non-polymer catechins in beverage | wt % | 0.152 | 0.148 | 0.05 | 0.151 |
| Total amount of total polyphenols in beverage | wt % | 0.189 | 0.167 | 0.062 | 0.187 |
| Color tone stability[6] of beverage |  | Good | Good | Good | Darkened |

[1]Green tea extract
"POLYPHENONE HG" (product of Tokyo Food Techno Co., Ltd.; 100 g) was dispersed in 38 wt % ethanol (420 g). A 92.5% aqueous ethanol solution (540 g) was added dropwise over 10 minutes. The resulting mixture was then subjected to aging under stirring for 30 minutes. Subsequent to the aging, coarse filtration was conducted with No. 2 filter paper. The filtrate was then filtered with filter paper having a 0.2 µm mesh to remove remaining insoluble components. To the resulting filtrate, water (200 mL) was added. Subsequent to concentration under reduced pressure, the concentrate was subjected to lyophilization.
The resultant green tea extract - the content of non-polymer catechins: 38 wt %, the content of total polyphenols: 44.7 wt %, non-polymer catechins/total polyphenols: 0.85.
[2]Green tea extract
"POLYPHENONE HG" (product of Tokyo Food Techno Co., Ltd.; 100 g) was dispersed in 99.5 wt % ethanol (630 g). Water (270 g) was added dropwise over 10 minutes. The resulting mixture was then subjected to aging under stirring for 30 minutes. Subsequent to the aging, coarse filtration was conducted with No. 2 filter paper. The filtrate was then filtered with filter paper having a 0.2 µm mesh to remove remaining insoluble components. To the resulting filtrate, water (200 mL) was added. Subsequent to concentration under reduced pressure, the concentrate was subjected to lyophilization.
The resultant green tea extract - the content of non-polymer catechins: 37 wt %, the content of total polyphenols: 40.6 wt %, non-polymer catechins/total polyphenols: 0.91.
[3]Green tea extract
"POLYPHENONE HG" (product of Tokyo Food Techno Co., Ltd.).
The content of non-polymer catechins: 33.70 wt %, the content of total polyphenols: 41.6 wt %, non-polymer catechins/total polyphenols: 0.81.
[4]Lyophilized product of green tea extract
Sencha (middle-grade green tea) leaves (40 g) were added to hot water (1,000 g) which had been heated to 90° C. With gentle stirring, extraction was conducted for 5 minutes. Subsequent to the extraction, filtration was conducted with double No. 2 filter paper, and the filtrate was promptly cooled to room temperature. The extract was lyophilized.
The resultant lyophilization product of the green tea extract - the content of non-polymer catechins: 33 wt %, the content of total polyphenols: 41 wt %.
[5]Commercially-available drinking water.
Quality marking - calcium content: 7.1 mg/100 mL, magnesium content: 2.4 mg/100 mL, sodium content: 4.7 mg/100 mL.
[6]Each packaged beverage which had been subjected to the post-treatment was left over at 55° C. for 1 week, during which the packaged beverage was observed for any change in appearance.
As a result of the 55° C. storage test of the packaged beverages, it turned out that despite the addition of non-polymer catechins at high concentration, the beverages of Examples 16-17 remained unchanged in color tone after the storage and were stable.
In Comparative Example 8, on the other hand, no particular problem arose because the content of non-polymer catechins was low. In Comparative Example 9, however, the beverage had a darker appearance with time.

What we claim is:

1. A green tea extract,
   wherein a content weight ratio [(A)/(B)] of (A) non-polymer catechins to (B) total polyphenols is from 0.83 to 0.96, and
   wherein a concentration of non-polymer catechins is from 35 to 55 wt %.

2. The green tea extract of claim 1, wherein:
   (a) a content of gallates in non-polymer catechins is from 45 to 60 wt %,
   (b) a weight ratio of said non-polymer catechins to caffeine is from 8 to 40,
   (c) a weight ratio of said non-polymer catechins to (sucrose+glucose) is from 2 to 15, and
   (d) dietary fibers amount to 0.5 wt % or less of a solid content.

3. The green tea extract of claim 1, wherein a content of gallates in the non-polymer catechins is from 45 to 60 wt %.

4. The green tea extract of claim 1, wherein a weight ratio of said non-polymer catechins to caffeine is from 8 to 40.

5. The green tea extract of claim 1, wherein a weight ratio of said non-polymer catechins to (sucrose+glucose) is from 2 to 15.

6. The green tea extract of claim 1, wherein dietary fibers, if present, amount to 0.5 wt % or less of a solid content.

7. A packed beverage, comprising a container and the green tea extract of claim 1.

8. The green tea extract of claim 1, comprising gallates and nongallates,
   wherein a content of the gallates is greater than a content of the nongallates.

* * * * *